(12) United States Patent
Quinn et al.

(10) Patent No.: US 8,663,268 B2
(45) Date of Patent: Mar. 4, 2014

(54) METHOD FOR ACCESSING THE LEFT ATRIAL APPENDAGE WITH A BALLOON-TIPPED TRANSSEPTAL SHEATH

(75) Inventors: Chris Quinn, Minneapolis, MN (US); Jin Shimada, Grantsburg, WI (US)

(73) Assignee: Atritech, Inc., Plymouth, MN (US)

( * ) Notice: Subject to any disclaimer, the term of this patent is extended or adjusted under 35 U.S.C. 154(b) by 0 days.

(21) Appl. No.: 13/403,420

(22) Filed: Feb. 23, 2012

(65) Prior Publication Data

US 2012/0157916 A1    Jun. 21, 2012

Related U.S. Application Data

(63) Continuation of application No. 11/607,769, filed on Dec. 1, 2006, now Pat. No. 8,142,470.

(60) Provisional application No. 60/741,113, filed on Dec. 1, 2005.

(51) Int. Cl.
*A61M 29/00* (2006.01)

(52) U.S. Cl.
USPC .......................................... 606/194; 606/200

(58) Field of Classification Search
USPC .......... 604/96.01, 103.05, 509, 528; 606/194, 606/200
See application file for complete search history.

(56) References Cited

U.S. PATENT DOCUMENTS

| | | | |
|---|---|---|---|
| 4,430,076 A * | 2/1984 | Harris ....................... | 604/103.03 |
| 5,690,611 A | 11/1997 | Swartz et al. | |
| 5,715,818 A | 2/1998 | Swartz et al. | |
| 5,814,029 A | 9/1998 | Hassett | |
| 5,820,591 A | 10/1998 | Thompson et al. | |
| 5,848,969 A | 12/1998 | Panescu et al. | |
| 5,882,340 A | 3/1999 | Yoon | |
| 5,984,946 A | 11/1999 | Gupta | |
| 6,090,084 A | 7/2000 | Hassett et al. | |
| 6,152,144 A | 11/2000 | Lesh et al. | |
| 6,650,923 B1 | 11/2003 | Lesh et al. | |
| 7,044,134 B2 | 5/2006 | Khairkhahan et al. | |
| 7,056,294 B2 | 6/2006 | Khairkhahan et al. | |
| 8,016,748 B2 * | 9/2011 | Mourlas et al. ............... | 600/115 |
| 2002/0035374 A1 * | 3/2002 | Borillo et al. .................. | 606/194 |
| 2002/0111647 A1 | 8/2002 | Khairkhahan et al. | |
| 2003/0144657 A1 | 7/2003 | Bowe et al. | |
| 2005/0038470 A1 | 2/2005 | Van der Burg et al. | |
| 2005/0148997 A1 | 7/2005 | Valley et al. | |
| 2006/0135962 A1 | 6/2006 | Kick et al. | |

FOREIGN PATENT DOCUMENTS

WO    0010452 A1    3/2000

* cited by examiner

*Primary Examiner* — Theodore Stigell
(74) *Attorney, Agent, or Firm* — Seager, Tufte & Wickhem LLC

(57) ABSTRACT

A method for accessing the left atrial appendage with a balloon-tipped transseptal sheath is disclosed. A transseptal sheath is delivered to the left atrium through the intraatrial septum from the right atrium. The balloon tip may be inflated to prevent the transseptal sheath from falling proximally into the right atrium. The inflated balloon tip permits safe probing and exploration of the left atrial appendage and facilitates safe maintenance of the position of the transseptal sheath within the left atrial appendage while delivering an implantable device to the left atrial appendage.

10 Claims, 27 Drawing Sheets

METHOD FOR ACCESSING THE LEFT ATRIAL APPENDAGE WITH A BALLOON-TIPPED TRANSSEPTAL SHEATH

CROSS-REFERENCE TO RELATED APPLICATIONS

This application is a continuation of U.S. application Ser. No. 11/607,769, filed Dec. 1, 2006, now U.S. Pat. No. 8,142,470, which claims the benefit of U.S. Provisional Application No. 60/741,113, filed Dec. 1, 2005, the entirety of which is hereby incorporated by reference.

BACKGROUND OF THE INVENTION

1. Field of the Invention

Embodiments of the present invention relate to delivery and retrieval of implantable devices, for example, to and from a left atrial appendage.

2. Description of the Related Art

Methods of percutaneously deploying left atrial appendage implants to the left atrial appendage of the heart are known to those of skill in the art. For example, one such method includes percutaneously delivering a non-steerable transseptal sheath to the right atrium of the heart, crossing the intraatrial Septum (IAS) with the transseptal sheath and a dilator, and after advancing the transseptal sheath through the IAS, withdrawing the dilator. When using such method it is often desired to advance the tip of the transseptal sheath as deep as possible into the left atrial appendage to assure that access to the left atrium is maintained.

However, to locate the left atrial appendage and direct the transseptal sheath thereto, these known methods typically use addition equipment and devices, such as: a J tip guidewire of varying stiffness, a pigtail catheter, and a transition catheter. Once the transseptal sheath has been advanced to the left atrial appendage, its morphology is assessed by injecting contrast and viewing under fluoroscopy. When the proper positioning has been confirmed, the additional equipment described above is then typically withdrawn from the vasculature. During equipment withdrawal the operator takes great care to assure that the transseptal sheath is not inadvertently moved and that access to the left atrium is maintained.

The implantable device is then typically deployed. If device recapture, retrieval and/or replacement is indicated, the transseptal sheath's position is maintained in the left atrium, the additional equipment and devices described above are re-deployed, and access to the left atrial appendage is re-established, as described above. When the implant is successfully deployed, final contrast injections are performed through sheath to assess implant condition. The transseptal sheath is then withdrawn.

When devices are advanced or withdrawn through the transseptal sheath forces are applied to the sheath wall. Such forces can cause the distal end of the transseptal sheath to become dislodged, moved or misaligned from its desired location. It would therefore be advantageous to be able to access the left atrial appendage and maintain access thereto without using additional equipment and devices.

SUMMARY OF THE INVENTION

In one embodiment, a method of delivering an implantable device to the left atrial appendage is provided. The method may comprise delivering a sheath to the left atrial appendage, inflating a distal end of the sheath within the left atrial appendage to anchor the distal end to tissue within the left atrial appendage, and delivering the implantable device through the sheath to the left atrial appendage.

In another embodiment, a method of delivering a device to an opening within a patient is provided. The method may comprise delivering a sheath to the opening, anchoring a distal end of the sheath to tissue adjacent the opening, and delivering a device through the sheath to the opening.

In another embodiment, a method of delivering an implantable device to the left atrial appendage is provided. The method may comprise delivering a sheath to the right atrium; advancing the sheath through the septum to the left atrium; inflating a distal end of the sheath, thereby providing the sheath with an atraumatic tip; positioning the distal end of the sheath adjacent the left atrial appendage; and delivering the implantable device through the sheath to the left atrial appendage.

All of these embodiments are intended to be within the scope of the present invention herein disclosed. These and other embodiments of the present invention will become readily apparent to those skilled in the art from the following detailed description of the preferred embodiments having reference to the attached figures, the invention not being limited to any particular preferred embodiment(s) disclosed.

DETAILED DESCRIPTION OF CERTAIN PREFERRED EMBODIMENTS

Embodiments of the present invention provide and maintain safe and easy access to the left atrial appendage ("LAA") of the heart for rapid and accurate deployment of an implantable device. Similar references numerals will be used to designate similar components in the different embodiments. Some embodiments of the present invention relate to a left atrial appendage implant that blocks and/or filters blood flow across the ostium of the LAA. One such implantable device and system is known to those of skill in the art as the PLAATO™ system from ev3 Inc. Additionally, some embodiments can include one or more features described in connection with one or more of the embodiments described herein.

Figure 1:
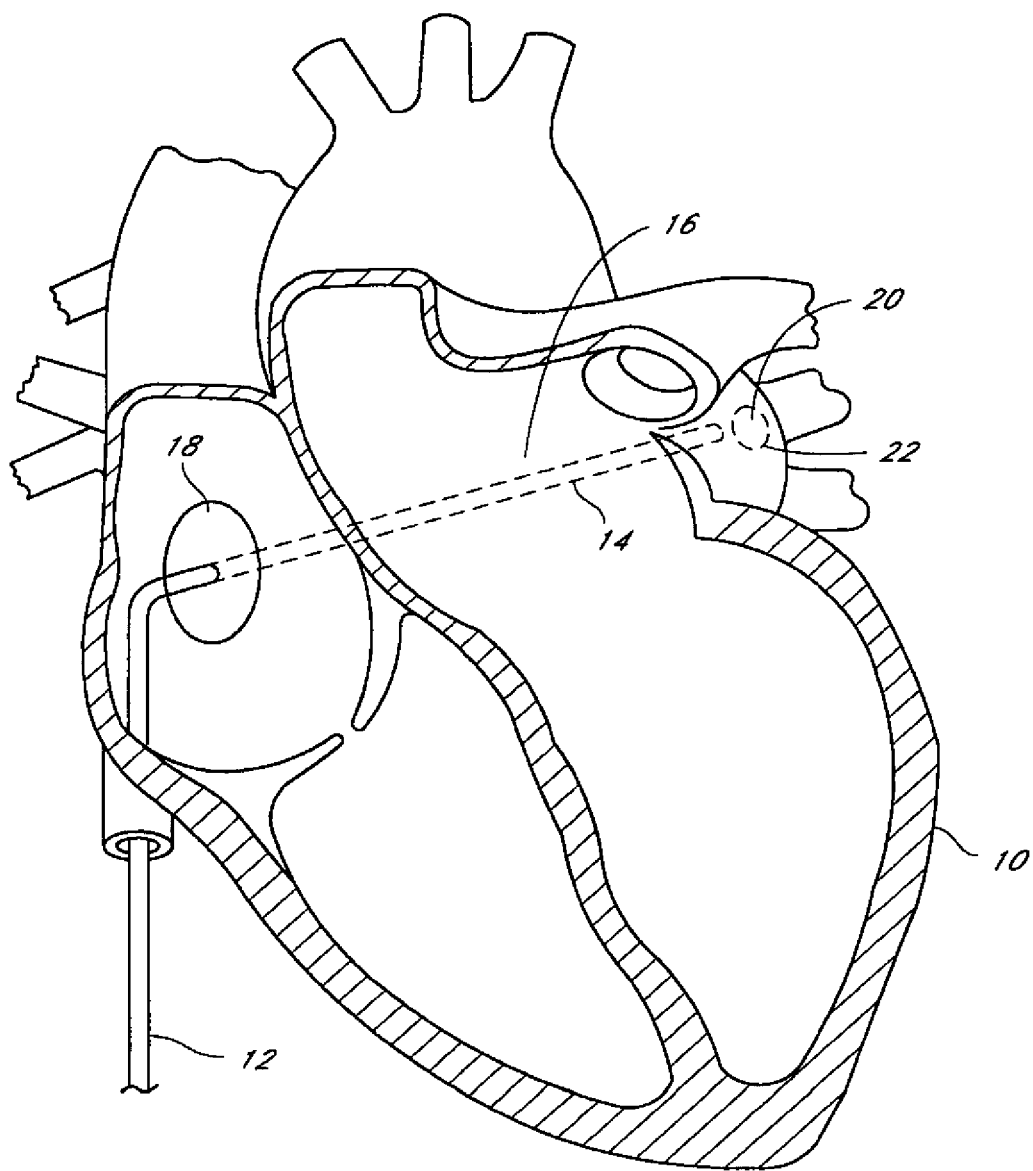
FIG. 1 is a schematic view of a patient's heart with a transseptal sheath deployed through the septum.
Figure 2:
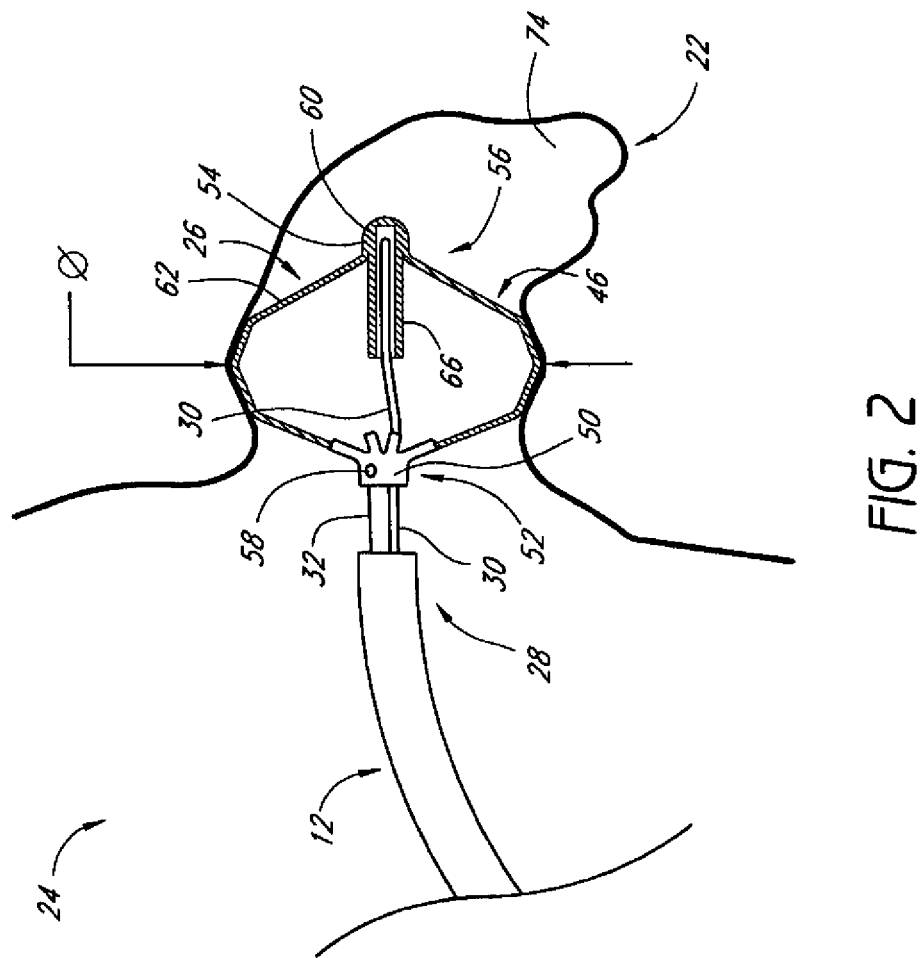
FIG. 2 is a schematic view of a deployment system delivering an implant to the left atrial appendage.

Referring to FIG. 1, a schematic view of a patient's heart 10 in partial section shows a transseptal sheath 12 having a distal end 14. The distal end 14 of the transseptal sheath 12 has breached the septum 18 of the patient's heart 10 and is disposed within the left atrium 16 adjacent the opening 20 of the patient's LAA 22. FIG. 2 illustrates a deployment system 24, having an implant 26 and a delivery system 28. The implant 26 may be designed to occlude or contain particles within the LAA 22 and prevent thrombus from forming in, and emboli from originating from, the LAA 22 in a patient with atrial fibrillation. The delivery system 28 preferably is compatible for use with the transseptal sheath 12. The delivery system preferably comprises an axially movable core 30 and a control wire 32. The delivery system 28 and implant 26 preferably are designed to allow the implant 26 to be positioned, repositioned, and retrieved from the LAA 22 if necessary.

The implant 26 preferably comprises a frame 46 and a membrane (not shown). The implant 26 preferably extends from a proximal hub 50 at a proximal end 52 increasing in diameter to an apex or apex portion, then decreasing to a distal hub 54 at a distal end 56. In some embodiments, the proximal hub 50 is coupled with a proximal crosspin 58. The distal hub 54 preferably is coupled with a plug or cap 60.

A plurality of supports 62 extend between a proximal hub 50 and a distal hub 54. In one embodiment, sixteen supports 62 are provided. However, the precise number of supports 62 can be modified, depending upon the desired physical properties of the implant 26 as will be apparent to those of skill in the art in view of the disclosure herein, without departing from the present invention.

Preferably, the supports 62 comprise a metal such as stainless steel, nitinol, Elgiloy, or others which can be determined through routine experimentation by those of skill in the art. The frame 46 preferably is constructed of self-expanding nitinol supports. Wires having a circular or rectangular cross-section may be utilized depending upon the manufacturing technique. In one embodiment, rectangular cross section supports are cut such as by known laser cutting techniques from tube stock, a portion of which forms the hubs 50 and 54.

In the illustrated embodiment, the distal end 56 of the implant 26 is provided with an implant plug or cap 60. In one embodiment, the implant plug 60 comprises an atraumatic tip, such that contact between the atraumatic tip and the inside surface of the LAA 22 does not cause significant damage to the LAA 22.

Various distal end 56 constructions may be utilized, as will be apparent to those of skill in the art in view of the disclosure herein. In the embodiment illustrated in FIG. 2, the plug 60 may be attached to a distal end of a distal guide tube 66, described in greater detail below. The plug 60 may be secured to the guide tube 66 and implant 26 in any of a variety of ways, depending upon the various construction materials. For example, any of a variety of metal bonding techniques such as a welding, brazing, interference fit such as threaded fit or snap fit, may be utilized. Alternatively, any of a variety of bonding techniques for dissimilar materials may be utilized, such as adhesives, and various molding techniques. In one construction, the plug 60 is composed of PEBAX.

The membrane (not shown) preferably is constructed of a fabric covering, such as one made of ePTFE, or an ePTFE/PE laminate. To attach the membrane to the frame 46, a PE mesh preferably is placed against the supports 62, with one sheet of ePTFE preferably placed over the PE mesh and another sheet of ePTFE preferably placed on an opposite side of the supports 62. The membrane preferably is heated on both sides causing the PE to melt into both sheets of ePTFE, thereby surrounding a portion of the frame 46. The nitinol supports allow the implant 26 to self-expand in the appendage 22, covering the orifice with the laminated fabric. The porous ePTFE/PE lamination facilitates rapid endothelialization and healing. The membrane preferably covers at least a proximal face of the device.

The core 30 may comprise any of a variety of structures which has sufficient lateral flexibility to permit navigation of the vascular system, and sufficient axial column strength to enable reduction of the implant 26 to its reduced crossing profile. Any of a variety of structures such as hypotube, solid core wire, "bottomed out" coil spring structures, or combinations thereof may be used, depending upon the desired performance of the finished device. In one embodiment, the core 30 comprises stainless steel tubing.

Referring to FIG. 2, the distal guide tube 66 extends proximally from the distal hub 54. The guide tube 66 receives the distal end of core 30 within a recess or lumen defined by the guide tube 66. Following positioning at or about the desired deployment site, proximal retraction of the core 30 enables the implant 26 to radially enlarge under its own bias to fit the surrounding tissue structure. The guide tube 66 may be a section of tubing such as metal hypotube, which is attached at the distal end 56 of the implant and extends proximally within the implant 26. The guide tube 66 preferably extends a sufficient distance in the proximal direction to inhibit buckling or prolapse of the core 30 when distal pressure is applied to the core to reduce the profile of the implant 26. However, the guide tube 66 should not extend proximally a sufficient distance to interfere with the opening of the implant 26.

As will be appreciated by reference to FIG. 2, the guide tube 66 may operate as a limit on distal axial advancement of the proximal end 50 of implant 26. Thus, the guide tube 66 preferably does not extend sufficiently far proximally from the distal end 56 to interfere with optimal opening of the implant 26. The specific dimensions are therefore relative, and will be optimized to suit a particular intended application. In one embodiment, the implant 26 has an implanted outside diameter within the range of from about 5 mm to about 45 mm, and an axial implanted length within the range of from about 5 mm to about 45 mm. The guide tube 66 may have an overall length of about 3 mm to about 35 mm, and an outside diameter of about 0.095 inches.

Further details regarding methods and apparatuses for accessing the LAA and LAA devices and related methods are disclosed in U.S. Pat. No. 7,056,294, filed Mar. 15, 2002; and U.S. patent application Ser. No. 10/642,384, filed Aug. 15, 2003 and published as U.S. Pat. Pub. No. 2005/0038470. The entirety of each of these is hereby incorporated by reference.

Figure 3:
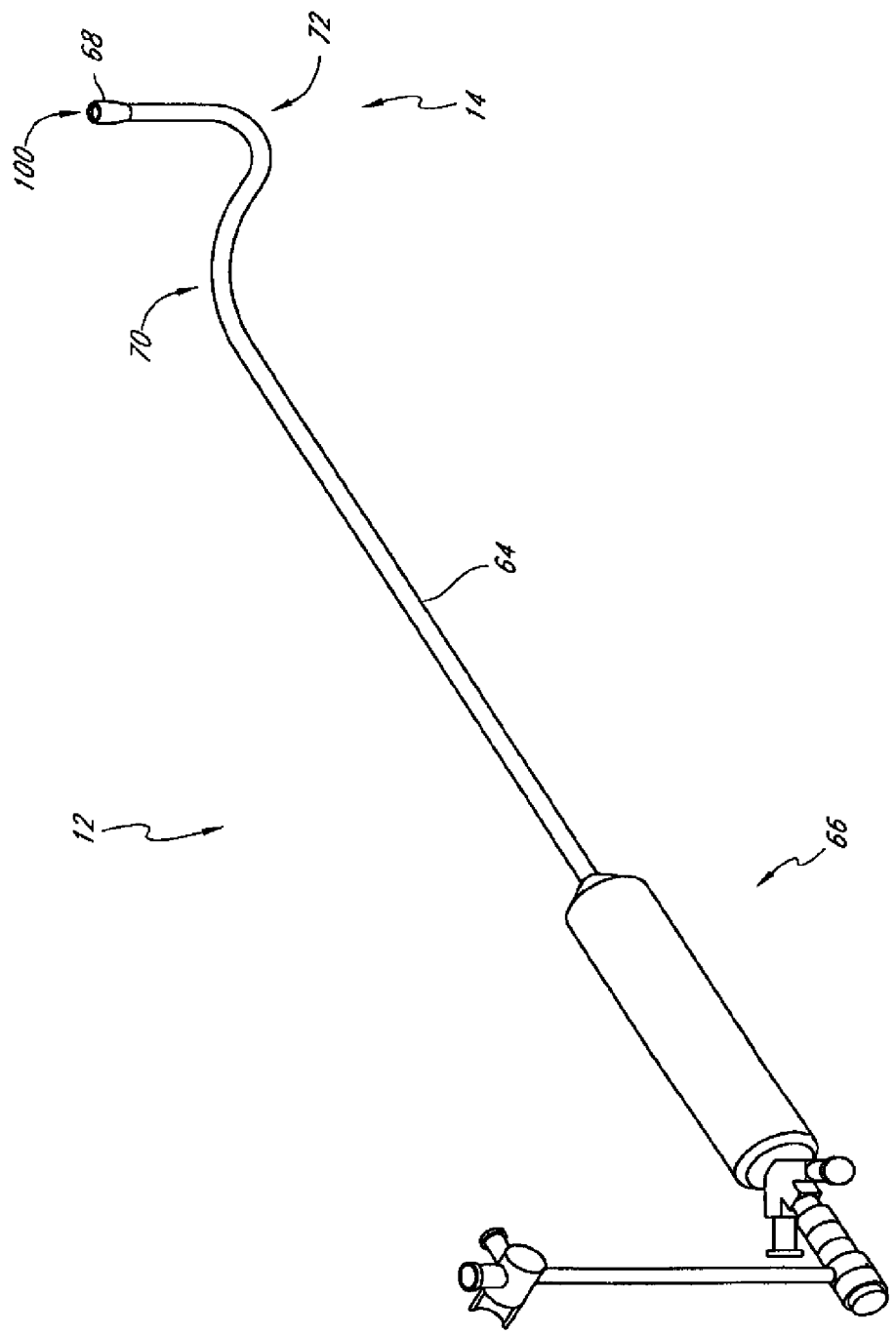
FIG. 3 is a perspective view of a steerable transseptal sheath with a balloon tip.

A transseptal sheath 12 is illustrated in FIG. 3. The transseptal sheath 12 may comprise an elongate, flexible tubular body 64, a control handle 66, and a balloon tip 68. In one embodiment, a tubular body 64 preferably is steerable using the handle 66 to facilitate access to the left atrium. The handle 66 may be coupled to a proximal end 80 of the sheath 12 to steer the distal end 14 of the transseptal sheath 12 and to control deployment and recapture of the implantable device. The handle 66 may be used to adjust the angulation, orientation, position, and/or pitch of the transseptal sheath 12. In some embodiments, the transseptal sheath may be designed to facilitate access to physiological structures, such as the LAA, the orifice of the LAA, the distal aspect of the LAA, or pulmonary vein such as the left superior pulmonary vein. One of ordinary skill in the art can determine the geometric orientation of the sheath that is suitable for any particular application based on the desired region of access and the particular patient's physiology through routine experimentation in view of the disclosure herein. In one embodiment that is useful for accessing regions of the LAA, a tubular body 64 may be steered such that the transseptal sheath 12 comprises a first curved section 70 to facilitate location of the fossa ovalis on the intraatrial septum and a second curved section 72 to facilitate location and access of the desired region of the LAA after penetration of the fossa ovalis. This may be accomplished by providing the sheath 12 with any of a variety of steering mechanisms, which allow a distal portion of the sheath to be inclined away from the axis of the normal bias of the catheter. For example, one or more axially moveable pull wires may extend through the length of the sheath. Proximal traction on a pull wire that is secured at a distal location of the catheter will cause a lateral deflection of the catheter. Other techniques will be known to those of skill in the art. Further details regarding steerable sheaths are disclosed in U.S. Pat. No. 7,056,294, filed Mar. 15, 2002, the entirety of which has been incorporated by reference.

Figure 4:
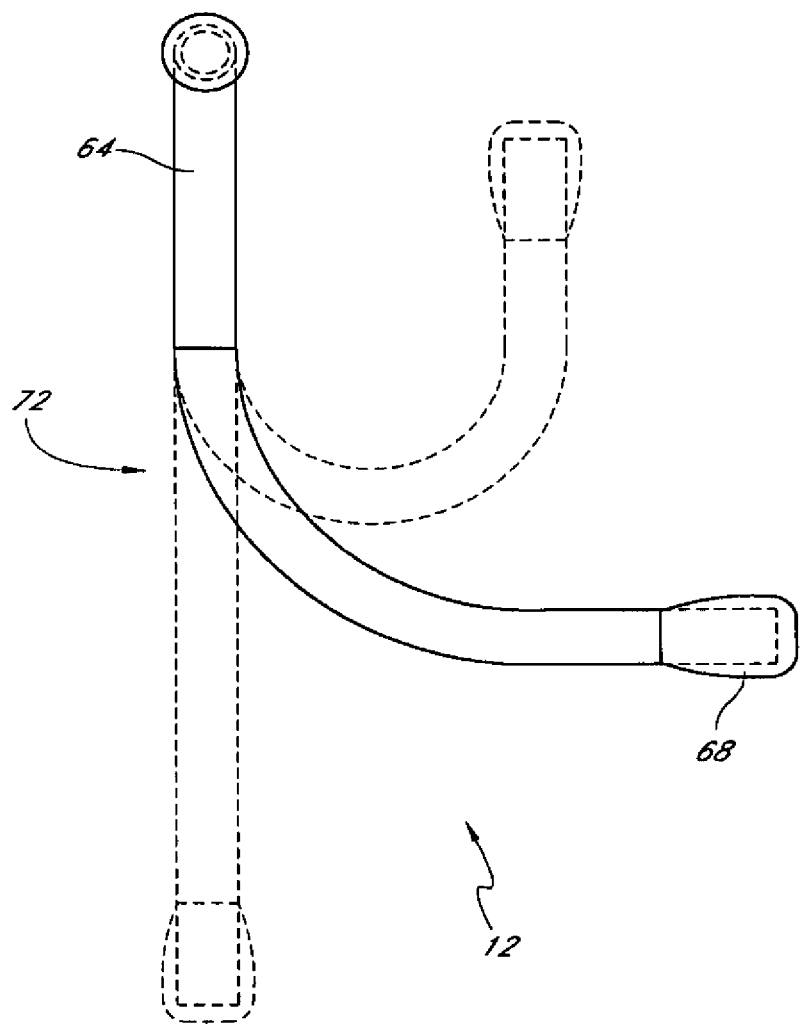
FIG. 4 is an enlarged schematic view of the distal end of the steerable transseptal sheath of FIG. 3.

One of ordinary skill in the art will recognize that the precise shape of these curves will depend on the patient's physiology and can be determined through routine experimentation. Accordingly, the first curved section 70 and the second curved section 72 may be steered through a range of angulations. For example, second curved section 72 may be steered through a range of angulations from about 0 .degree. to about 180 .degree., as shown in FIG. 4.

Typically, the location of a non-steerable transseptal sheath is maintained using a super stiff J tip wire. Use of a steerable sheath permits use of a lighter, less traumatic wire, or even delivery and positioning of the transseptal sheath without any guidewire, saving time and effort. It also helps reduce the possibility of sheath content embolization during multiple swapping of internal catheters prior to implant system introduction. A steerable transseptal sheath may have a thicker sheath wall than a non-steerable sheath to accommodate a steering wire and a balloon inflation lumen, and this thicker sheath wall is more robust and resilient. This is helpful for maintaining spatial orientation during left atrial appendage implant introduction and manipulation. It also increases column strength of the sheath during high loading conditions, such as recapture. In one embodiment, the wall of the transseptal sheath may be about 3 mm thick.

Figure 5:
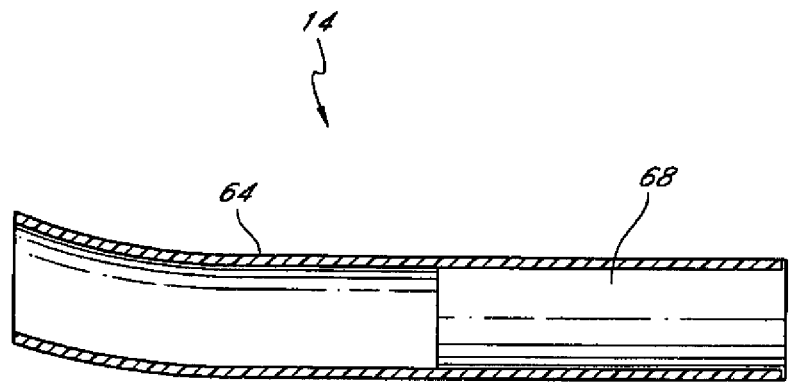
FIG. 5 is a partial cross sectional view of the balloon tip of FIG. 3 in a deflated state.
Figure 6:
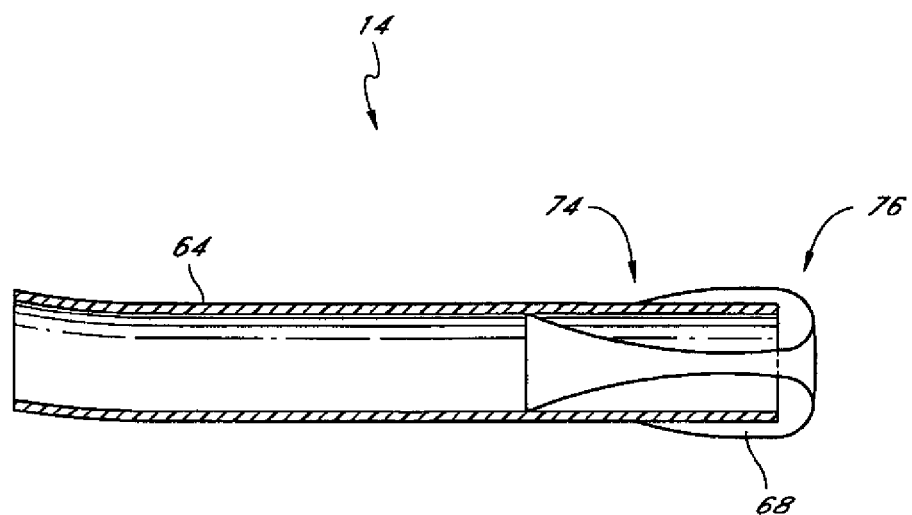
FIG. 6 is a partial cross sectional view of the balloon tip of FIG. 5 in an inflated state.

The balloon tip 68 may provide an atraumatic end 100 to sheath 12 to avoid damage to the anatomy when they contact each other. Referring to FIG. 4, the balloon tip 68 preferably is located at a distal end 14 of the transseptal sheath 12. In a deflated state the balloon tip 68 may have an inner diameter and an outer diameter generally equal to those of the tubular body 64, as shown in FIG. 5. When inflated, the balloon tip 68 may have a maximum outer diameter larger than the outer diameter of the tubular body 64, a minimum inner diameter smaller than the inner diameter of the tubular body 64, or both, as illustrated in FIG. 6. The balloon tip 68 may inflate to an outer diameter of about 4 mm or less to about 30 mm or more. In one embodiment, the balloon may inflate to an outer diameter of about 6 mm. The balloon tip 68 when inflated may have a larger diameter near a distal end 76 than near a proximal end 74. In another embodiment, the balloon tip may inflate to a diameter as large as or slightly larger than that of the left atrium.

The balloon tip 68 may be about 3 mm or less to about 12 mm or more long. In one embodiment the balloon tip 68 may be about 10 mm long. The interior length and the exterior length may be different. In one embodiment, the interior length is about 10 mm while the exterior length is about 5 mm. Alternatively, the exterior length may be greater than the interior length. The balloon tip 68 may also increase in length when it is inflated. The length may increase by about 1 mm or less to about 3 mm or more. In one embodiment, the balloon tip 68 may increase in length by about 1.5 mm when inflated. The inflated balloon tip 68 may extend distally from the tubular body 64 to soften the distal end 14 of the sheath 12, as shown in FIG. 6. The distal extension of the balloon tip 68 from the tubular body 64 may correspond to the increase of the balloon's length when it is inflated. It should also be appreciated that the balloon tip 68 may be inflated to a size smaller than its maximum size.

Figure 7:
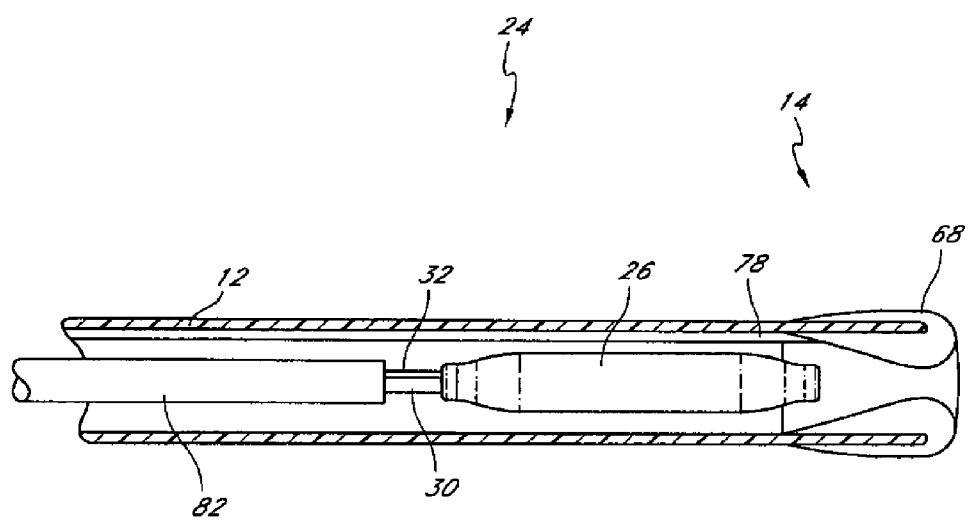
FIG. 7 is a schematic view of an implant deployment system.

The sheath may comprise a channel or lumen 78 for inflating the balloon tip 68, as shown schematically in FIG. 7. In one embodiment, the balloon tip 68 may be inflated with saline. In another embodiment, the balloon tip 68 may be inflated with fluid comprised of radiopaque fluid such as contrast media. The balloon may be made from any of a variety of materials well known to those of skill in the art, including latex, polyurethane, polymers, rubber, PEBAX, or any other known elastic material. In one embodiment, the balloon is made from silicone rubber.

The deployment system 24, shown schematically in FIG. 7, may comprise a transseptal sheath 12, a balloon tip 68, a delivery catheter 82, an axially movable core 30, a control wire 32, and an implant 26 (shown schematically). Details of the deployment system and implant are described in U.S. patent application Ser. No. 10/642,384, filed Aug. 15, 2003 and published as U.S. Pat. Pub. No. 2005/0038470, the entirety of which has been incorporated by reference. The balloon tip 68 may be connected to a distal end 14 of the sheath 12. The delivery catheter 82 may be disposed within the sheath 12. The axially movable core 30 and the control wire 32 may extend through the delivery catheter 82 and connect to the implantable device 26. The deployment system 24 may be used to deploy the implant 26 within a LAA.

To deliver the system, a preferred access point is along the right femoral vein, although access from the left femoral vein is also possible. Access may also be achieved through a puncture in any of a variety of other veins of suitable internal diameter and the present invention is not limited in this regard.

A conventional spring tipped guidewire is thereafter advanced through the needle into the vein and the needle is subsequently removed. A dilator preferably is positioned within a transseptal or outer sheath of the type described herein, or other well-known sheaths, such as a 14 French introducer sheath. Subsequently, the transseptal sheath and dilator, in combination with the guidewire, are advanced through the femoral vein to the right atrium.

Figure 8:
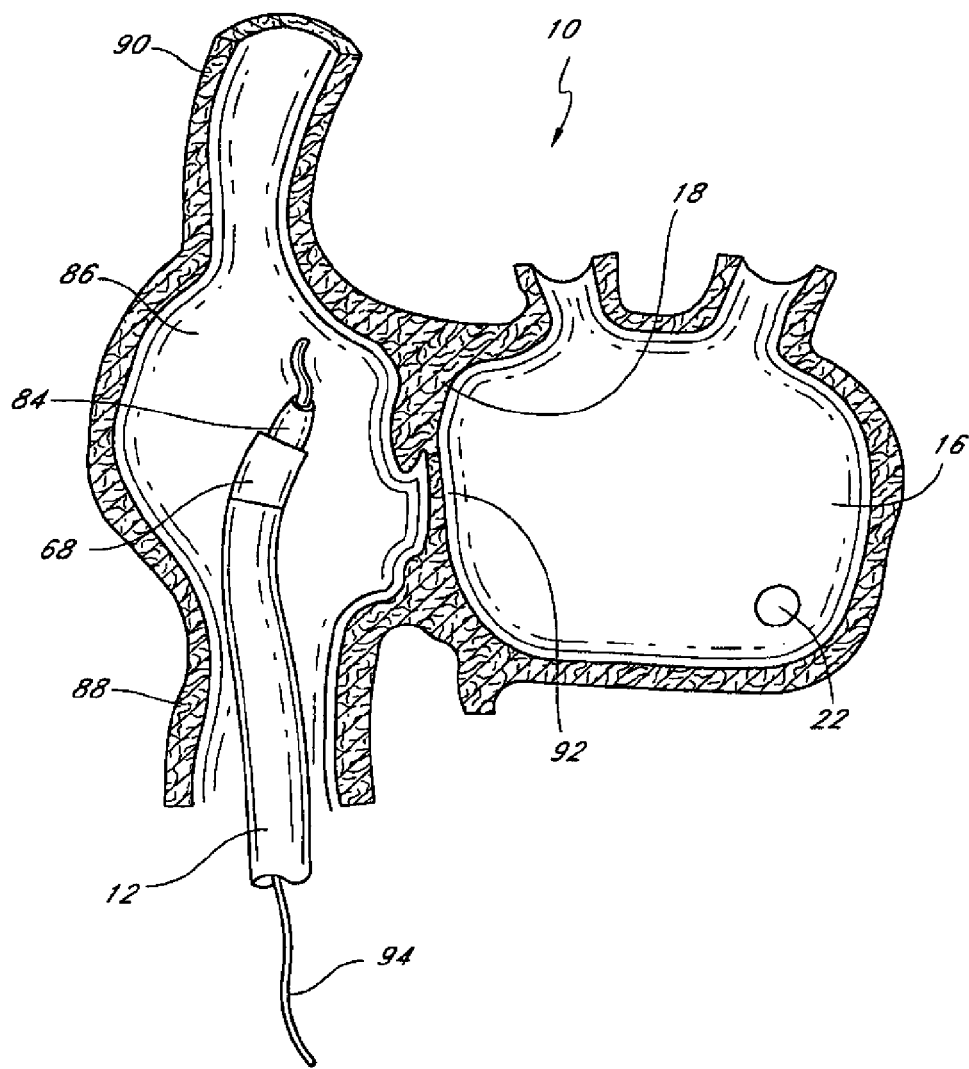
FIG. 8 is a schematic cross-sectional view of a portion of the heart, showing a transseptal sheath of one embodiment of the present invention within the right atrium.

Referring to FIG. 8, there is illustrated a schematic cross-section of a portion of the heart 10. The right atrium 86 is in communication with the inferior vena cava 88 and the superior vena cava 90. The right atrium 86 is separated from the left atrium 16 by the intraatrial septum 18. The fossa ovalis 92 is located on the intraatrial septum 18. As seen in FIG. 8, the transseptal sheath 12 may have the dilator 84 and a guidewire 94 therein, may be positioned within the right atrium 86. In one embodiment, the transseptal sheath has an inside diameter of about 12 Fr and an outside diameter of about 15 Fr. The transseptal sheath wall thickness is about 1 mm. In other embodiments, the transseptal sheath wall thickness is about 0.5 mm, about 1.5 mm, or about 2 mm. In some embodiments the transseptal sheath wall thickness is not more than about 2.5 mm.

Figure 9:
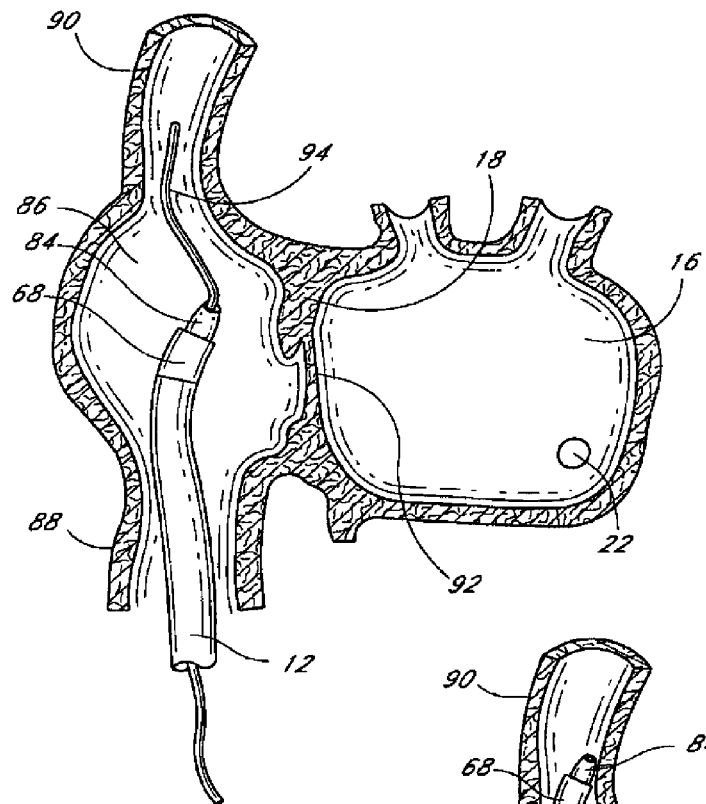
FIG. 9 is a cross-sectional view as in FIG. 8, with the guidewire positioned in the superior vena cava.

The guidewire 94 is thereafter distally advanced to access the superior vena cava 90. See FIG. 9. The dilator 84 and sheath 12 are thereafter advanced into the superior vena cava as illustrated schematically in FIG. 10. The guidewire 94 may be proximally retracted. An advantage of embodiments of the present invention is that the transseptal sheath may be steered to a desired location independent of other components or devices. In addition, the sheath may be steered either with or without the implantable device being located therein.

When the sheath 12 and the dilator 84 are in the superior vena cava 90 and the guidewire 94 has been removed if one has been employed, a transseptal needle 96 may be advanced through the dilator 84 and sheath 12. The transseptal needle 96 is advanced (possibly with a stylet in place) to a point that the stylet tip is just inside the distal tip of the sheath 12 and dilator 84, a position previously noted by the operator, and the stylet is withdrawn from the transseptal needle.

Figure 10:
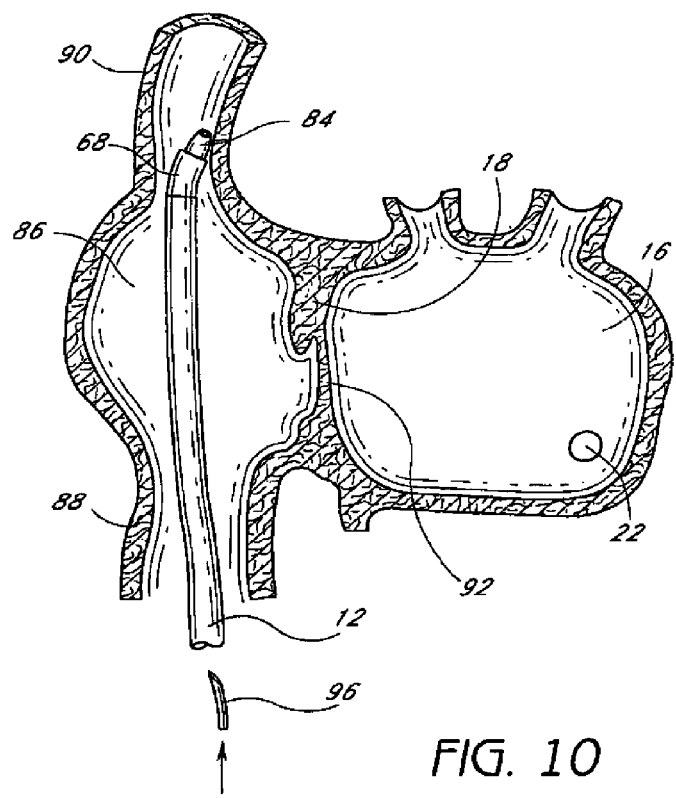
FIG. 10 is a cross-sectional view as in FIG. 8, with the transseptal sheath positioned against the wall of the superior vena cava.
Figure 11:
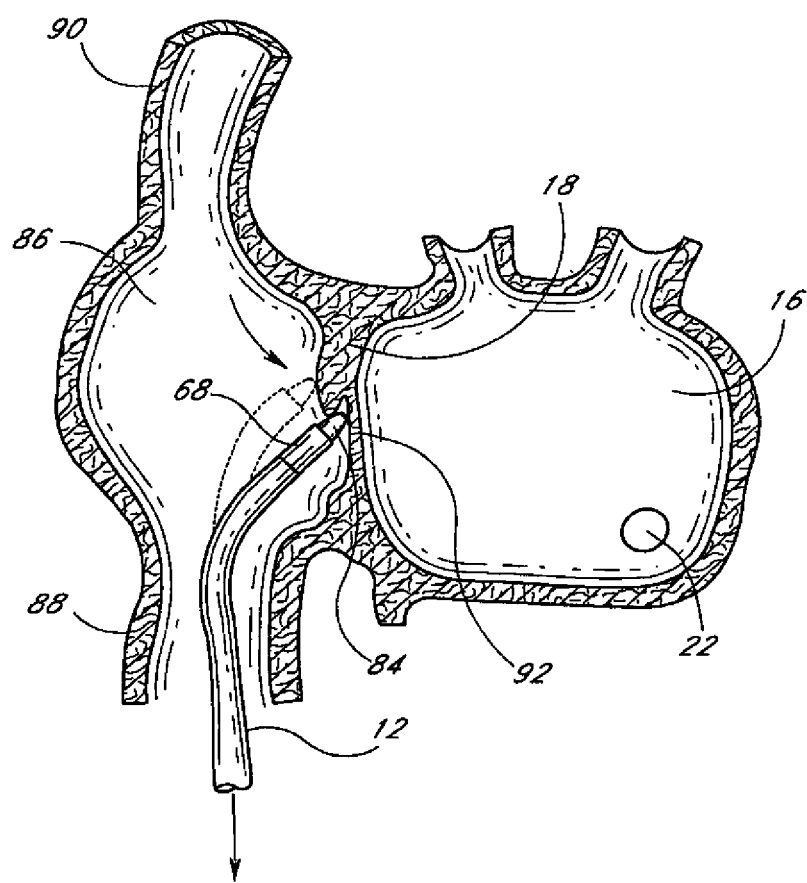
FIG. 11 is a cross-sectional view as in FIG. 8, with the transseptal sheath positioned against the fossa ovalis.

The remaining combination of the sheath 12 with the dilator 84 having the transseptal needle 96 therein, is then drawn proximally from the superior vena cava while the first curved section 70 of the sheath, alone or in combination with a preset curve at the distal region of dilator 84, causes the tip of the sheath-dilator-transseptal needle combination to "drag" along the wall of the right atrium 86 and the septum 18, as illustrated in FIGS. 10 and 11.

The tip of the dilator 84 is then positioned against the septum 18 by distal advancement through the sheath 12. The tip is then dragged along the septum by proximal traction on the dilator 84 until the tip pops onto the fossa ovalis 92, as shown in FIG. 11.

The physician is normally assisted during placement, as in the entire procedure, by fluoroscopy or other visualization techniques. To assist in such visualization, the distal tip of sheath 12 and the distal tip of dilator 84 may be provided with a radiopaque marker. In addition, some physicians find it desirable to infuse a radiopaque dye through the transseptal needle 96 at various stages of the procedure to assist in visualization, particularly following the transseptal puncture.

Figure 12:
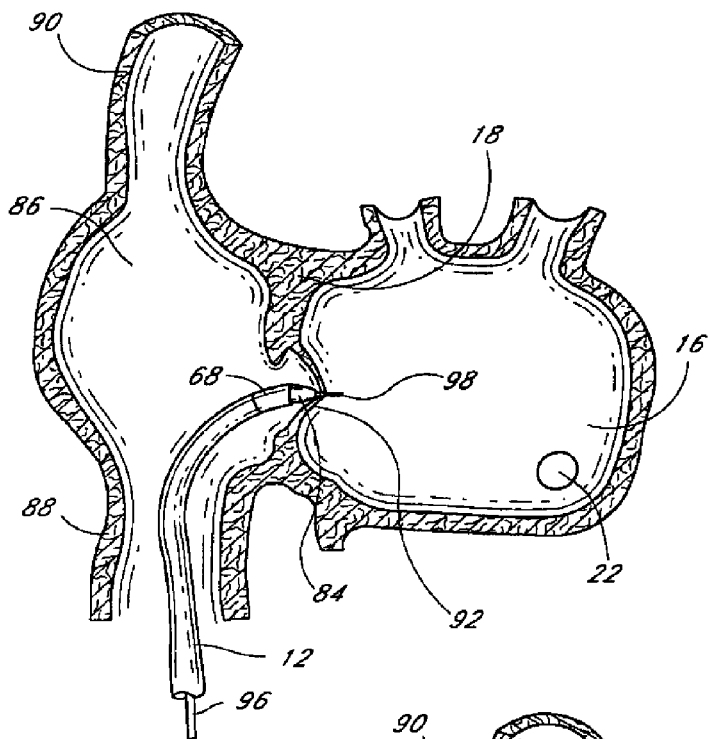
FIG. 12 is a cross-sectional view as in FIG. 8, showing tissue distention or "tenting" as the needle punctures the fossa ovalis.

After the tip of the sheath-dilator-transseptal needle combination has been placed in the desired location against the fossa ovalis 92, the transseptal needle 96 is abruptly advanced to accomplish a quick puncture (see FIG. 12). In one embodiment the needle is advanced by applying a force to the proximal end of the needle. In this embodiment the needle often comprises a stiff proximal section and a flexible distal section. The distal section preferably comprises ribbon coil.

Immediately after the puncture, one medical technique is to confirm the presence of the tip 98 of the transseptal needle 96 within the left atrium 16. Confirmation of such location of the tip 98 of the transseptal needle 96 may be accomplished by monitoring the pressure sensed through the transseptal needle lumen to ensure that the measured pressure is within the expected range and has a waveform configuration typical of left atrial pressure. Alternatively, proper position within the left atrium 16 may be confirmed by analysis of oxygen saturation level of the blood drawn through the transseptal needle 96; i.e., aspirating fully oxygenated blood. Finally, visualization through fluoroscopy alone, or in combination with the use of dye, may also serve to confirm the presence of the tip 98 of the transseptal needle 96 in the left atrium 16.

Figure 13:
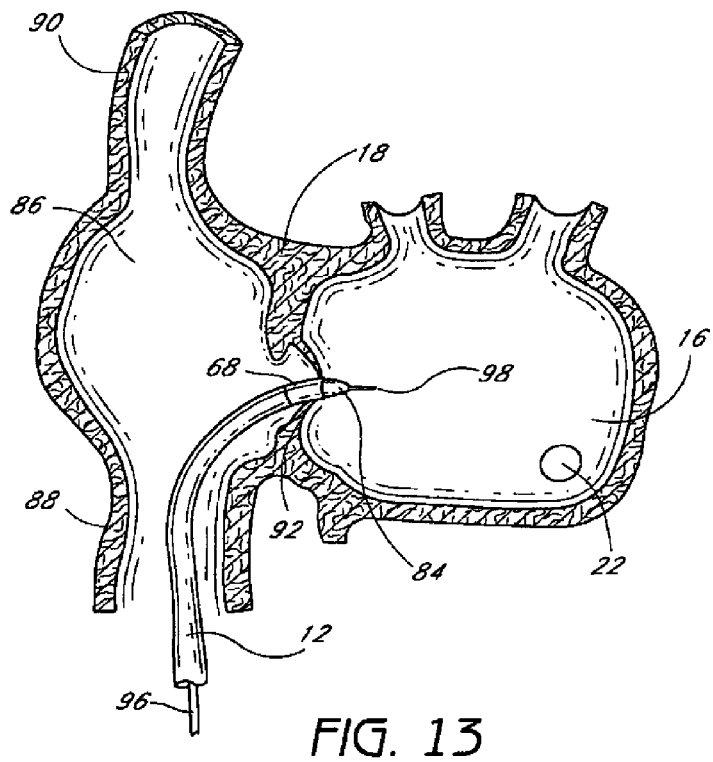
FIG. 13 is a cross-sectional view as in FIG. 12, showing tissue distention as the dilator is advanced through the fossa ovalis.
Figure 14:
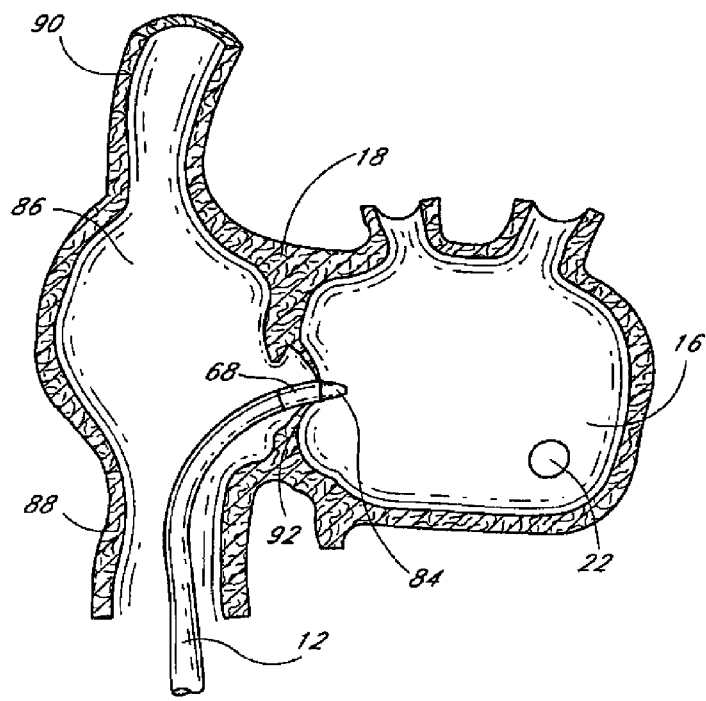
FIG. 14 is a cross-sectional view as in FIG. 13, illustrating the transseptal sheath, which has been advanced over the dilator and through the septum.
Figure 15:
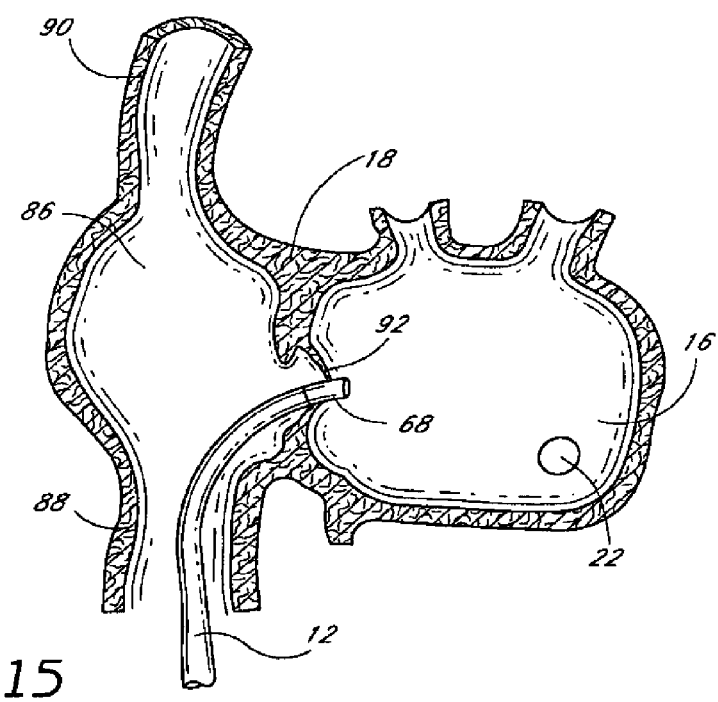
FIG. 15 is a cross-sectional view as in FIG. 14, with the dilator removed, leaving the transseptal sheath in place across the fossa ovalis.

After placing the transseptal needle tip 98 within the left atrium 16, the tip of the dilator 84 is advanced through the septum 18 and into the left atrium 16, as shown in FIG. 13. Typically, care is taken to ensure that, at the same time of advancing the dilator and sheath tip into the left atrium, the tip of the transseptal needle is not advanced a sufficient distance that the needle 96 can damage the opposing wall of the left atrium 16. When the tapered tip of dilator 84 appears to have entered the left atrium 16, the transseptal needle 96 is withdrawn. The sheath 12 is then advanced into the left atrium 16, either by advancing the sheath 12 alone over the dilator 84 or by advancing the sheath 12 and dilator 84 in combination (see FIG. 14). The dilator 84 is then withdrawn from sheath 12 when the latter has been advanced into the left atrium, thus leaving the main lumen of sheath 12 as a clear pathway to advancing further diagnostic or therapeutic instruments into the left atrium, as shown in FIG. 15.

It will be appreciated that other techniques may be used to deliver a transseptal sheath to the left atrium or to other locations in the body. For example, the sheath need not pass through the fossa ovalis, but may be delivered through another portion of the septum.

Figure 16:
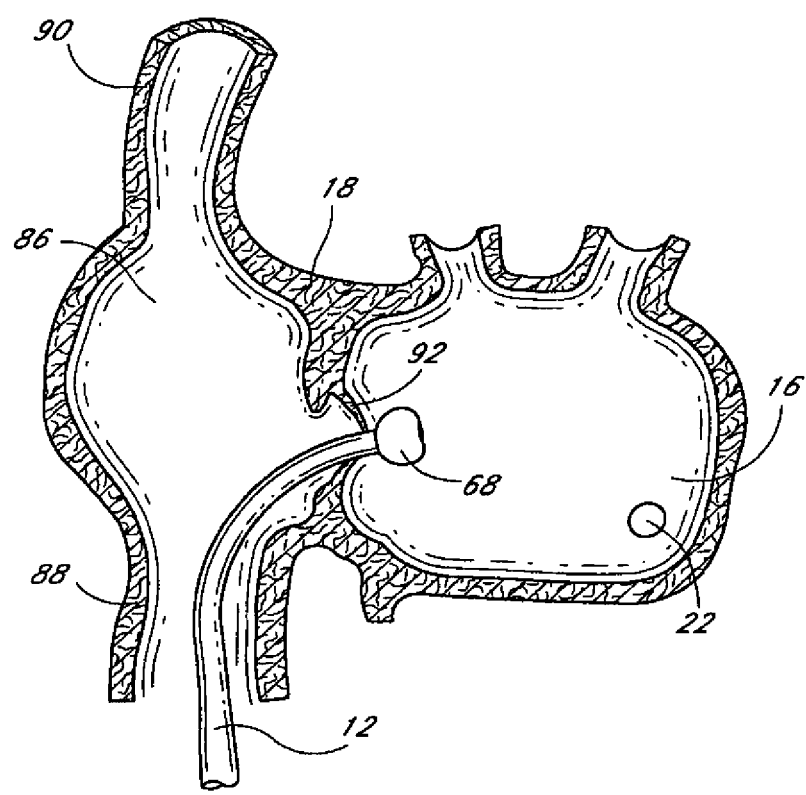
FIG. 16 is a cross-sectional view as in FIG. 15, with the transseptal sheath in place across the fossa ovalis and the balloon tip inflated.

In one embodiment, illustrated in FIGS. 8-16, the sheath 12 comprises an inflatable balloon 68 at the distal end 14 and means for inflating the balloon 78 (see FIG. 7), such as an inflation lumen. The balloon 68 preferably is in a deflated position as the sheath 12 crosses the fossa ovalis 92 to access the left atrium. The balloon tip 68 may be inflated after it crosses the fossa ovalis 92, as shown in FIG. 16. In those embodiments where the balloon 68 is inflated to a diameter greater than the diameter of the sheath 12, the balloon 68 prevents the sheath from unintentionally passing back through the fossa ovalis during subsequent procedures. The inflated balloon 68 creates an atraumatic distal tip that can be navigated to access a location of interest, such as the LAA, without use of any additional device or catheters to blunt the edge of the transseptal sheath 12. The balloon tip 68 may be inflated to a diameter of about 4 mm or less to about 12 mm or more. In one embodiment, the balloon tip 68 is inflated to a diameter of about 6 mm to prevent the sheath from passing back through the septum and to provide an atraumatic tip for probing the LAA.

Figure 17:
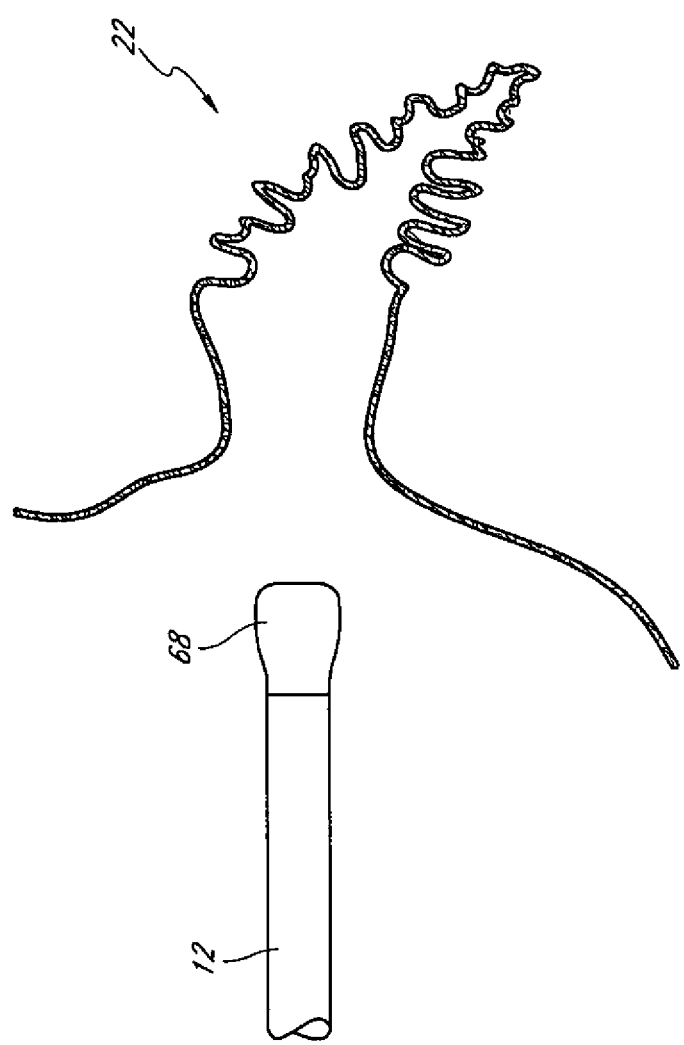
FIG. 17 is a schematic cross-sectional view of a left atrial appendage, showing a transseptal sheath with an inflated balloon tip within the left atrium near the left atrial appendage.
Figure 18:
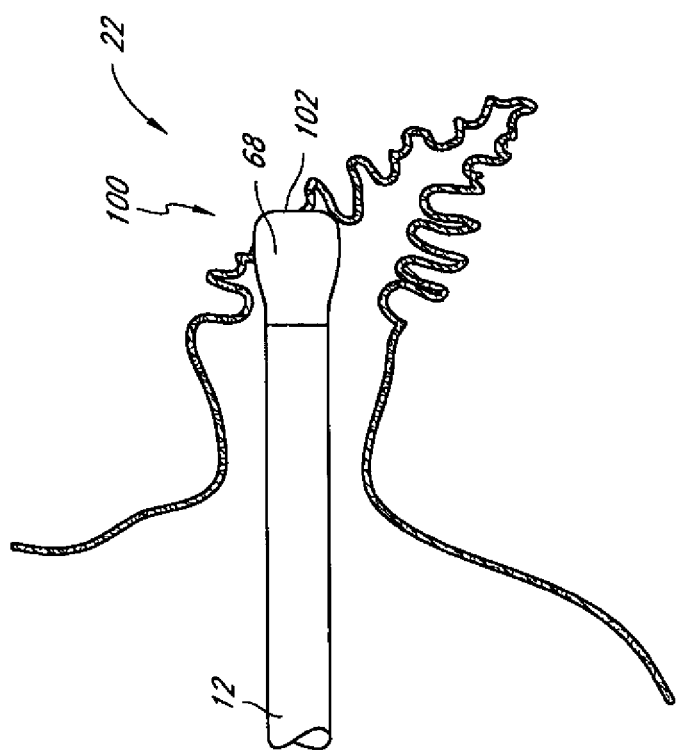
FIG. 18 is a cross-sectional view as in FIG. 17, with the transseptal sheath positioned centrally within the left atrial appendage.

Referring to FIG. 17, the transseptal sheath 12, with the balloon 68 inflated, may be advanced to the LAA 22. In one embodiment, a steerable transseptal sheath 12 may be advanced into the LAA without use of a guidewire. In another embodiment, the transseptal sheath 12 may be advanced into the LAA by guiding it over a guidewire. The balloon tip 68 allows the transseptal sheath 12 to be used for LAA access, visualization and probing, including mechanical probing or "feeling out" the inside wall of the heart, as illustrated in FIG. 18, without causing trauma. When steerable transseptal sheath 12 and a balloon tip 68 are used careful probing over a guidewire, a pigtail catheter and transition catheter are unnecessary. This is an advantage as it is known, when using guidewires, to puncture the LAA membrane with sequelae such as cardiac tamponade, epicardial perfusion, or other adverse events.

The balloon tip 68 may generally comprise an atraumatic end 100 to prevent trauma to the inside wall of the LAA 22 during deployment, anchoring, and advancement of the implantable device 26. The atraumatic end 100 can be the distal surface 102 of the balloon tip 68, or it can be an atraumatic surface attached to the distal surface 102 of the balloon tip 68. The atraumatic end 100 can be made from any of a variety of materials well known to those of skill in the art, including latex, polyurethane, polymers, rubber, plastic, PEBAX, or any other known atraumatic material. In one embodiment the atraumatic end is made from silicone.

Once the distal end of the transseptal sheath is in the LAA, the LAA's morphology is assessed. For example, the morphology can be assessed by injecting contrast into the left atrial appendage and viewing the heart under fluoroscopy. More than one lobe is present in the LAA more than 60% of the time. In one embodiment, a steerable transseptal sheath 12 may be used to explore multiple locations within the LAA to ascertain the morphology of the LAA and determine the optimal and/or desired implant location.

Figure 19:
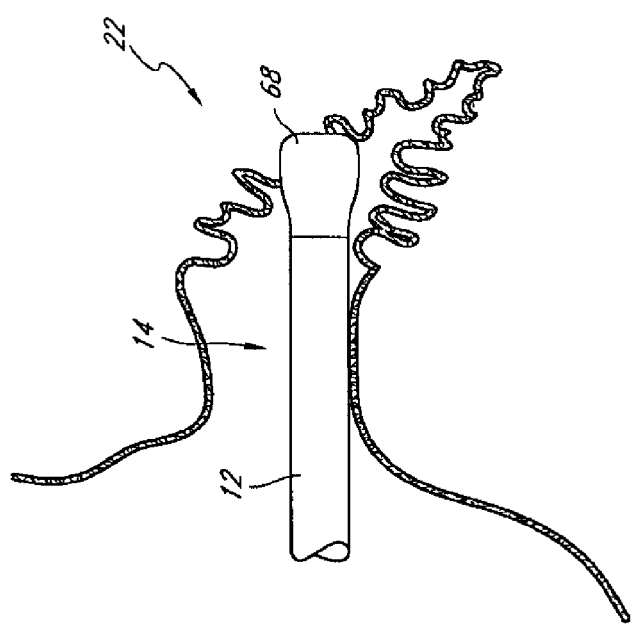
FIG. 19 is a cross-sectional view as in FIG. 17, with the transseptal sheath positioned deeply within the left atrial appendage.

The transseptal sheath 12 may be secured in place by pressing or wedging the inflated balloon tip 68 of the transseptal sheath 12 into the narrow wall of the left atrial appendage, as shown in FIG. 19. The balloon tip 68 may be further inflated to maintain the transseptal sheath 12 in the LAA 22 during equipment exchange through sheath lumen. This avoids the possibility of the transseptal sheath 12 accidentally exiting the LAA 22 or the left atrium during implantable device delivery. In this manner, the outer sheath can be anchored in place without piercing or otherwise cutting, poking, or pinching the inside wall of the heart, including the inside wall of the atria, ventricles, or atrial appendages. Anchoring the outer sheath in place facilitates imaging of the appendage by way of injection of radiopaque materials followed by techniques such as fluoroscopy.

Once the desired location for implant delivery has been identified and the distal end 14 of the transseptal sheath 12 has been secured in place, the implantable device may be introduced into the transseptal sheath 12. Alternatively, the implantable device may have been preloaded into the transseptal sheath. The position of the transseptal sheath 12 preferably is maintained while advancing the implantable device through the transseptal sheath 12 to the LAA 22. If the distal end 14 of the transseptal sheath 12 shifts or is otherwise moved out of the desired location it may be steered back to the proper position.

Figure 20:
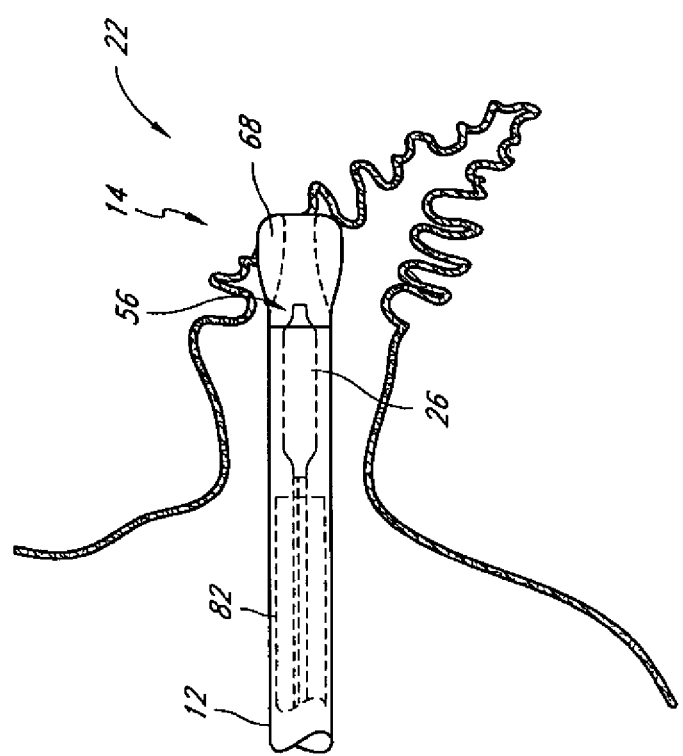
FIG. 20 is a cross-sectional view as in FIG. 19, with an implant positioned within the transseptal sheath near the distal end.
Figure 21:
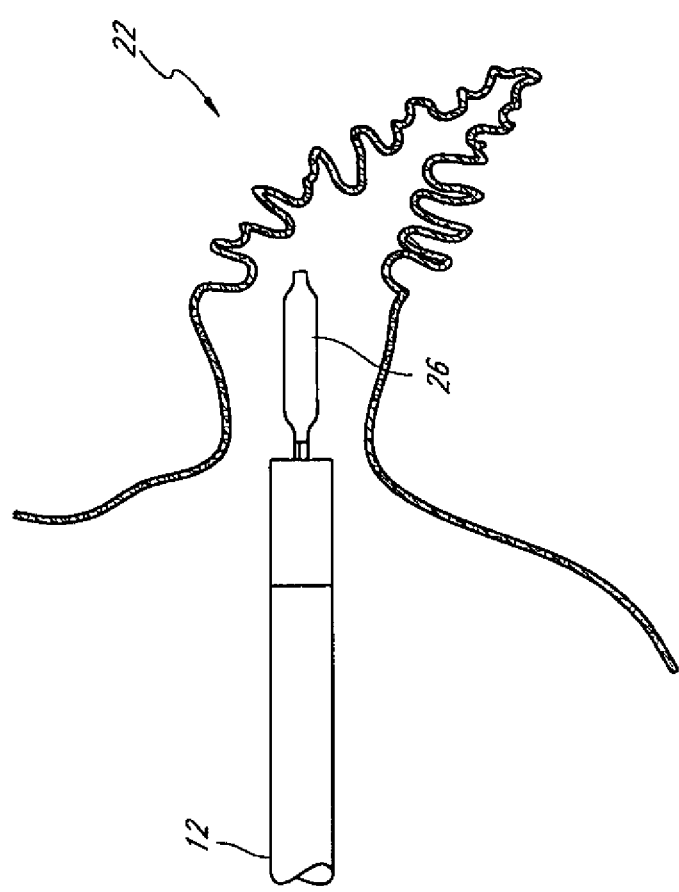
FIG. 21 is a cross-sectional view as in FIG. 20, with the implant positioned within the left atrial appendage, the balloon tip deflated, and the transseptal sheath retracted proximally.

Referring to FIG. 20, the implantable device 26 may be advanced until its distal end 56 is within about 2 mm or less to about 10 mm or more from the distal end 14 of the sheath 12. In one embodiment the implantable device 26 is advanced within about 5 mm of the distal end 14 of the sheath 12. When in position, the balloon tip 68 may be deactivated so it no longer locks the distal end 14 of the sheath 12 within the LAA 22. Alternatively, the balloon tip 68 may remain inflated. The sheath 12 may then be retracted proximally to expose the implantable device 26, as illustrated in FIG. 21.

Figure 22:
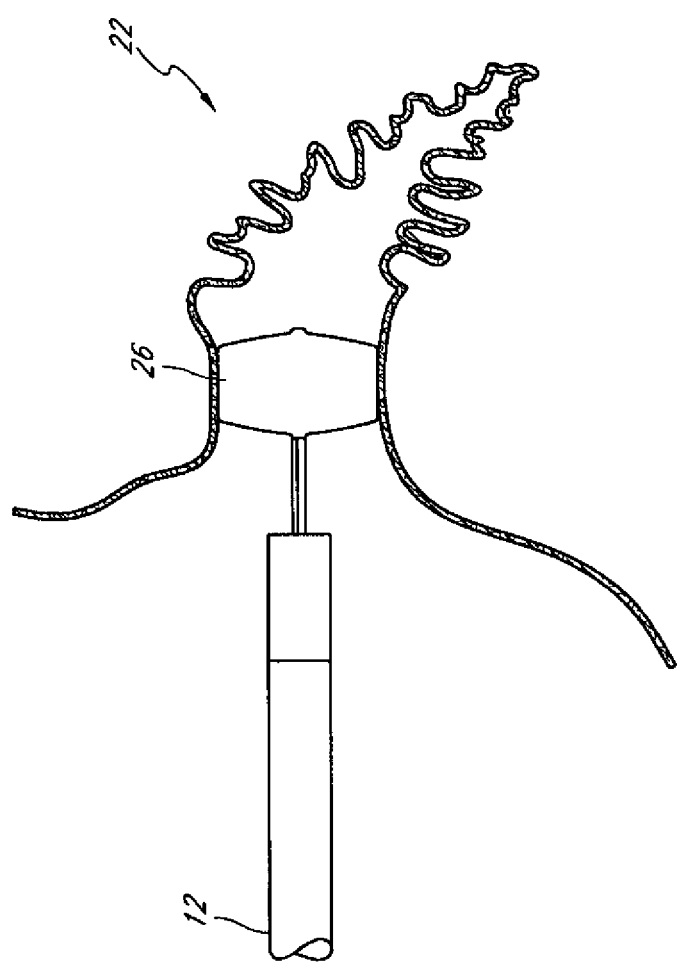
FIG. 22 is a cross-sectional view as in FIG. 21, with the implant expanded within the left atrial appendage.

The implantable device 26 may then be deployed, as shown in FIG. 22, using any of a variety of mechanisms known to those of skill in the art. In some embodiments, the implantable device 26 is self-expanding, and expands upon retraction of the sheath 12. If a self-expanding implantable device is used, the implantable device 26 preferably is positioned in the desired location before refraction of the sheath 12.

Figure 23:
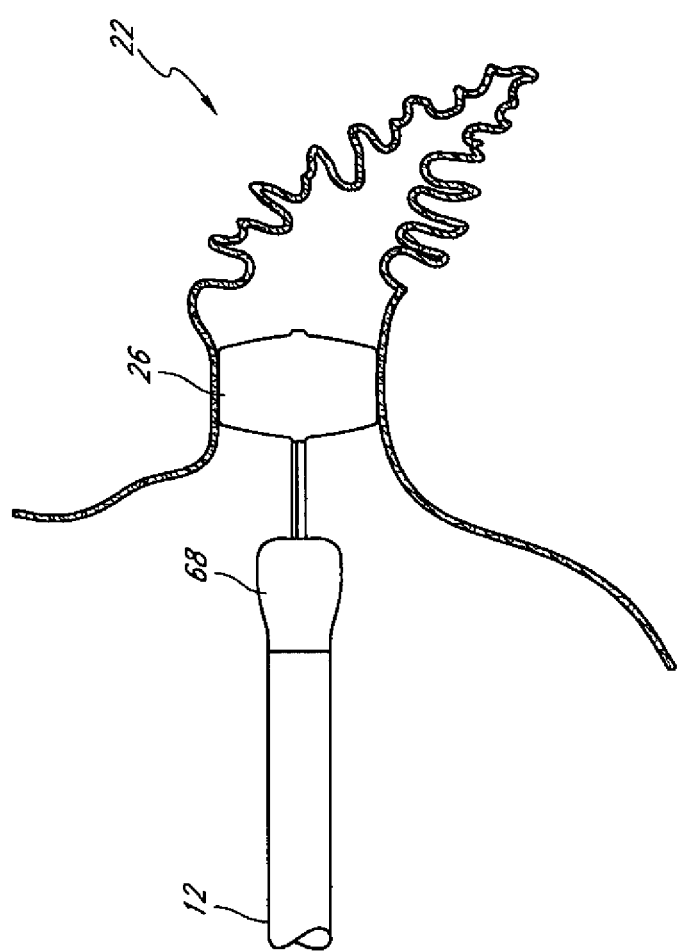
FIG. 23 is a cross-sectional view as in FIG. 22, with the balloon tip inflated.

If it is desired to recapture, replace, and/or retrieve the implantable device 26 once deployed, the distal end 14 of transseptal sheath 12 may be maintained in the left atrium by inflating the balloon tip 68 (see FIG. 23). The inflated balloon tip 68 may thereby provide an atraumatic stop that does not pass proximally septum 18 into the right atrium 86 (see FIG. 16).

When the implantable device appears to have been successfully positioned at the desired location, final contrast injections may be provided through the transseptal sheath to assess the implant's condition. The transseptal sheath may be steered to various locations within the heart to allow for complete fluoroscopic assessment. The balloon tip maybe inflated at this time to provide an atraumatic interface between the transseptal sheath's distal end and the inner wall of the heart. When assessment is completed the balloon tip 68 is returned to its reduced-diameter configuration, and the transseptal sheath is withdrawn from the patient's body. If necessary, access to the LAA can be re-established according to the method described above.

Figure 24:
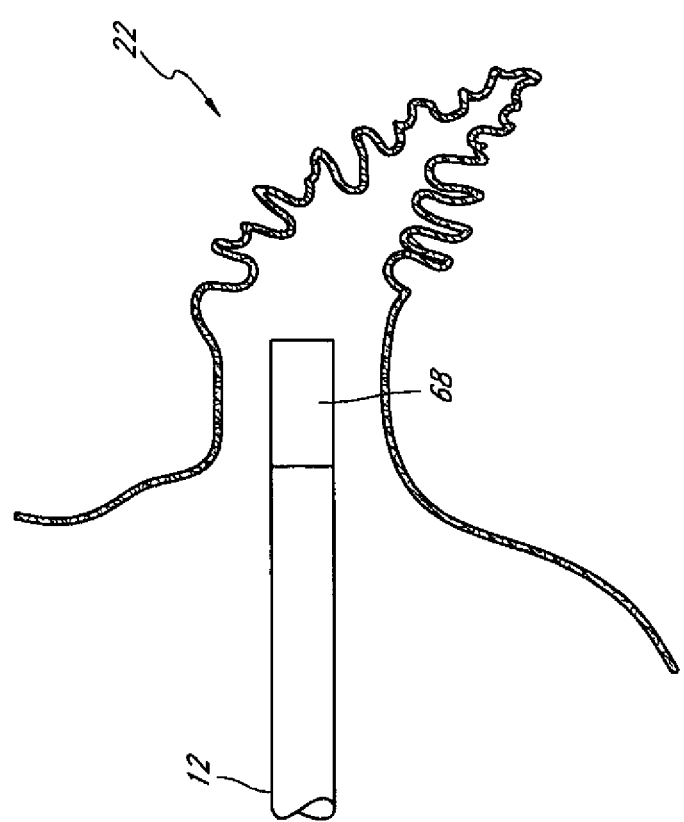
FIG. 24 is schematic cross-sectional view of a left atrial appendage, showing a transseptal sheath with a deflated balloon tip within the left atrial appendage.
Figure 25:
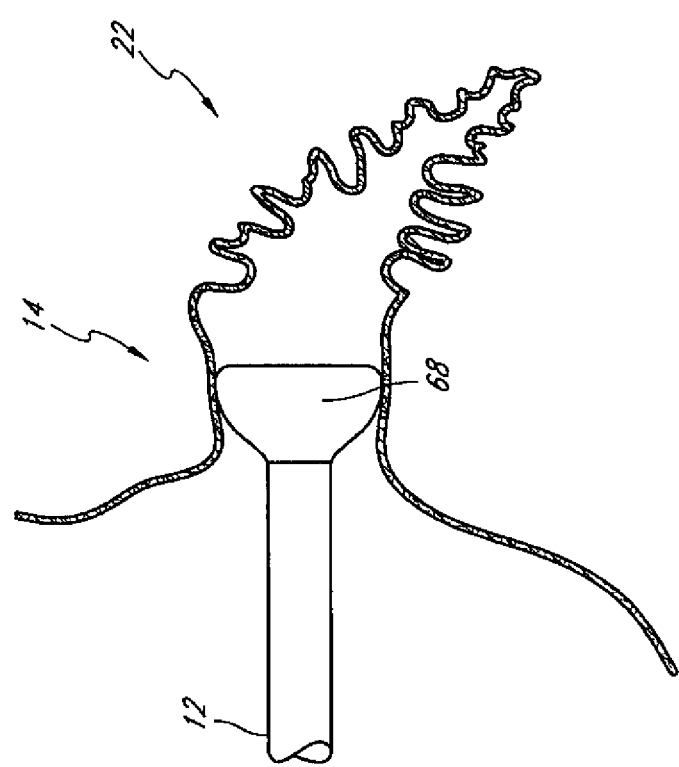
FIG. 25 is a cross-sectional view as in FIG. 24, with the balloon tip inflated to anchor the transseptal sheath within the left atrial appendage.

In another embodiment, the transseptal sheath 12 may be inserted into the LAA 22 with the balloon tip 68 deflated, as illustrated in FIG. 24. Once at the deployment site, the balloon tip 68 is inflated to secure the distal end 14 of the sheath 12 in place during advancement of the implantable device 26 through the outer sheath, as shown in FIG. 25. In one embodiment, the balloon tip 68 is inflated to a diameter of about 24 mm to secure the distal end 14 of the sheath 12 in LAA 22. In some embodiments, the balloon tip 68 may comprise ribs, hooks, barbs, anchors, bands, rings, or other friction devices to secure the distal end of the outer sheath in place when activated.

Figure 26A:
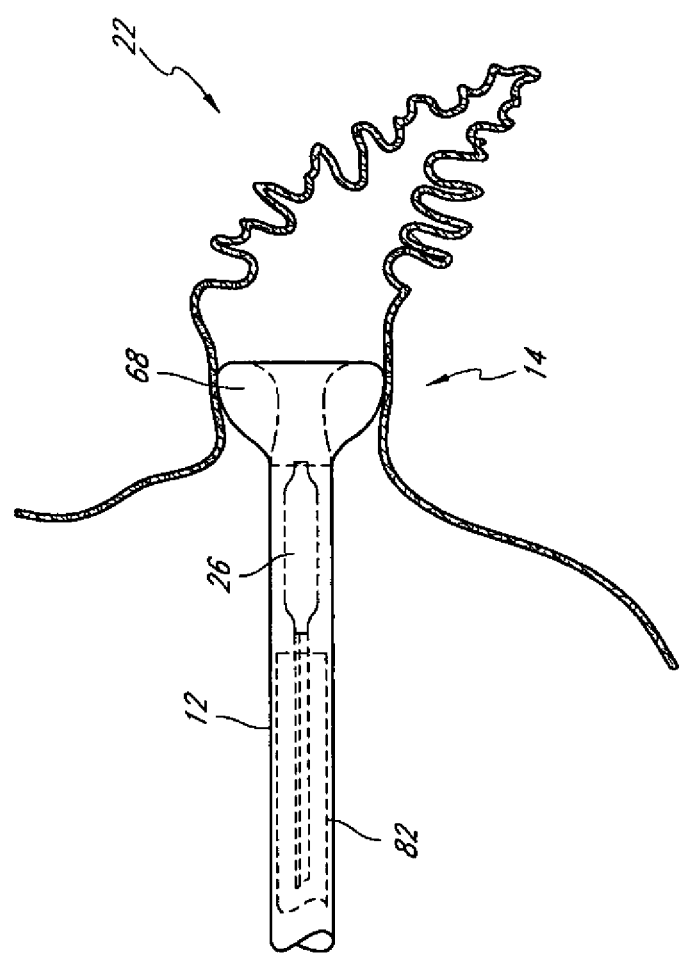
FIG. 26A is a cross-sectional view as in FIG. 25, with an implant positioned within the transseptal sheath near the distal end.
Figure 26B:
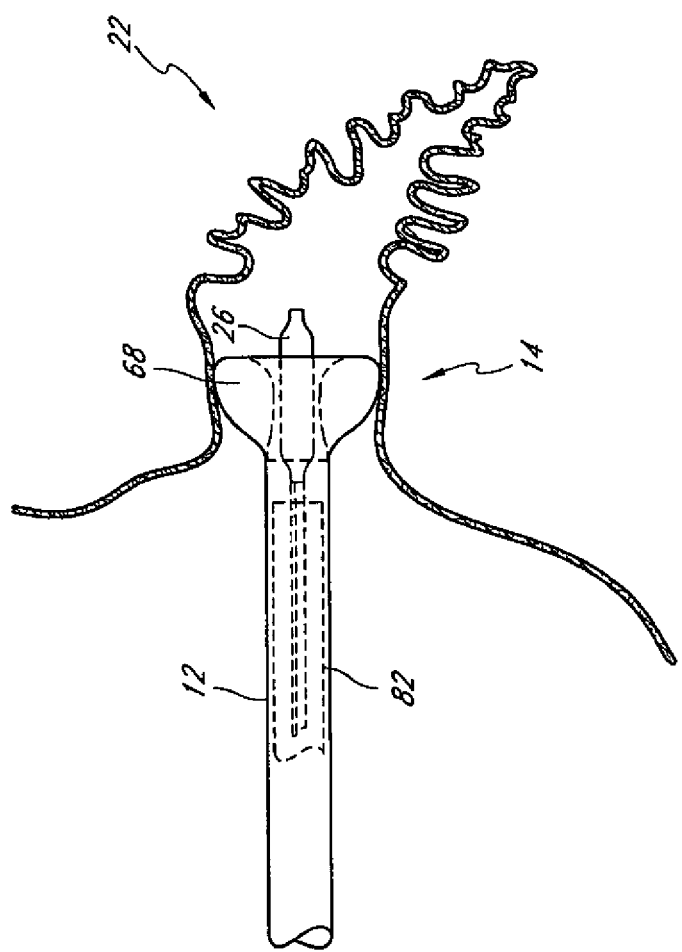
FIG. 26B is a cross-sectional view as in FIG. 25, with an implant partially protruding from the distal end of the transseptal sheath.

Once the sheath 12 has been anchored in place with the balloon tip 68, the delivery catheter 82 advances the implantable device 26 through the sheath 12, as shown in FIG. 26A. The implantable device 26 may be advanced until its distal end 56 is within about 2 mm or less to about 30 mm or more beyond distal end 14 of the sheath 12, as illustrated in FIGS. 26A and 26B. In one embodiment the implantable device 26 preferably is advanced within about 10 mm or more from the distal end 14 of the sheath 12, and more preferably within about 8 mm of the distal end 14 of the sheath 12. Positioning of the implantable device 26 within the sheath 12 and within the heart may be confirmed by any visualization technique known to those of skill in the art. For example, in one embodiment, the position of the implant 26 is determined by fluoroscopy or another imaging technique.

Figure 27:
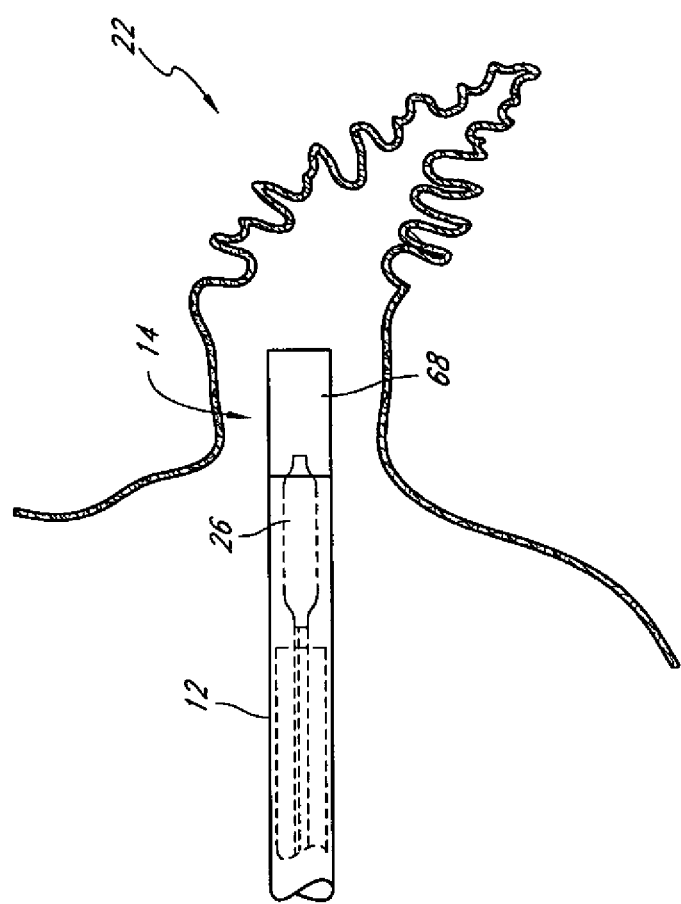
FIG. 27 is a cross-sectional view as in FIG. 25, with a balloon tip deflated.
Figure 28A:
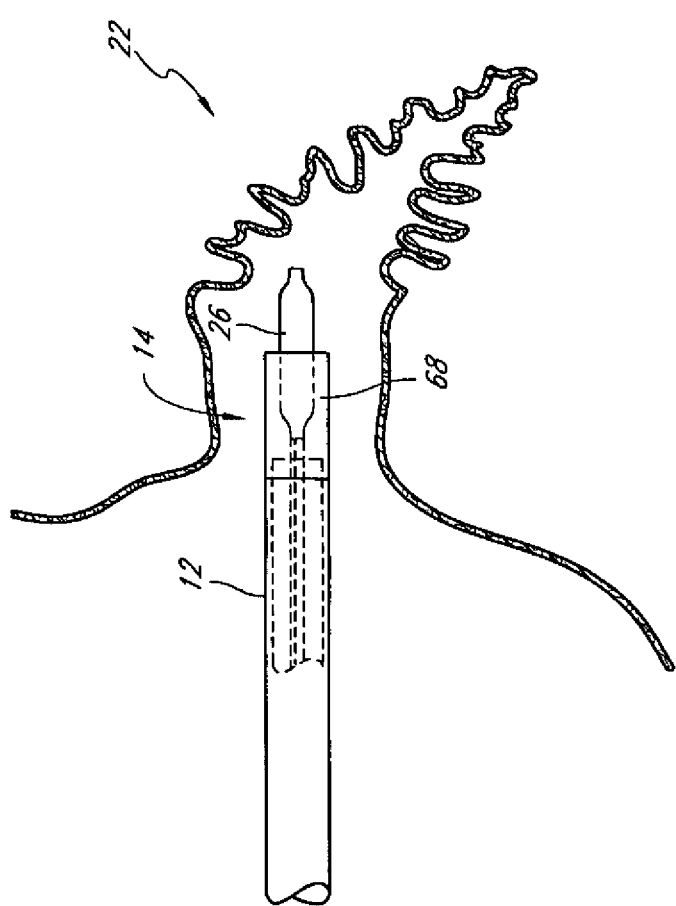
FIG. 28A is a cross-sectional view as in FIG. 25, with an implant partially protruding from the distal end of the transseptal sheath.
Figure 28B:
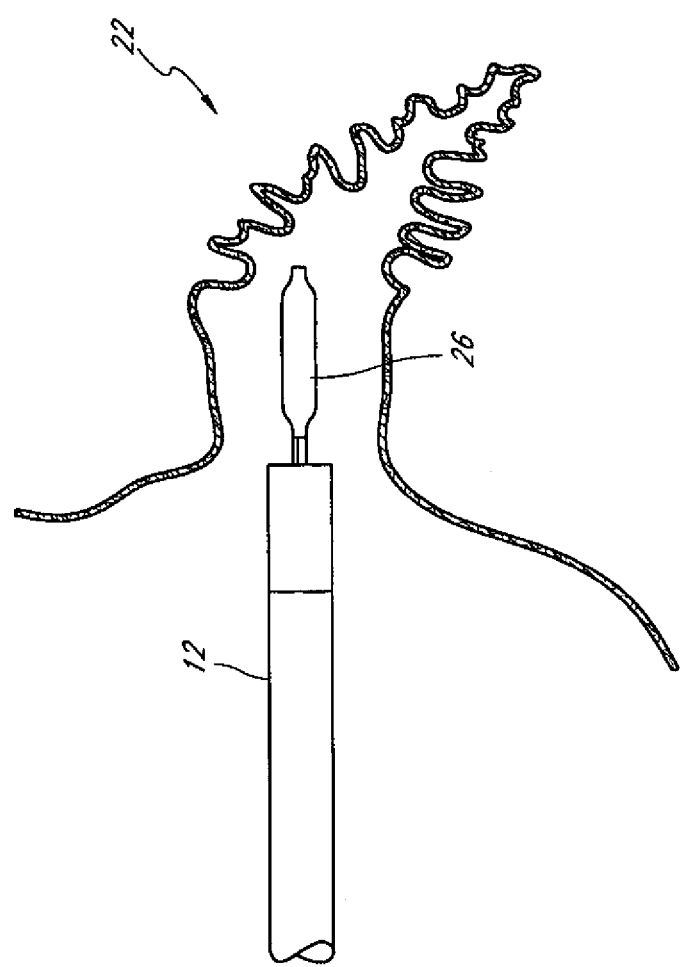
FIG. 28B is a cross-sectional view as in FIG. 25, with the implant positioned within the left atrial appendage and the transseptal sheath retracted proximally.
Figure 29:
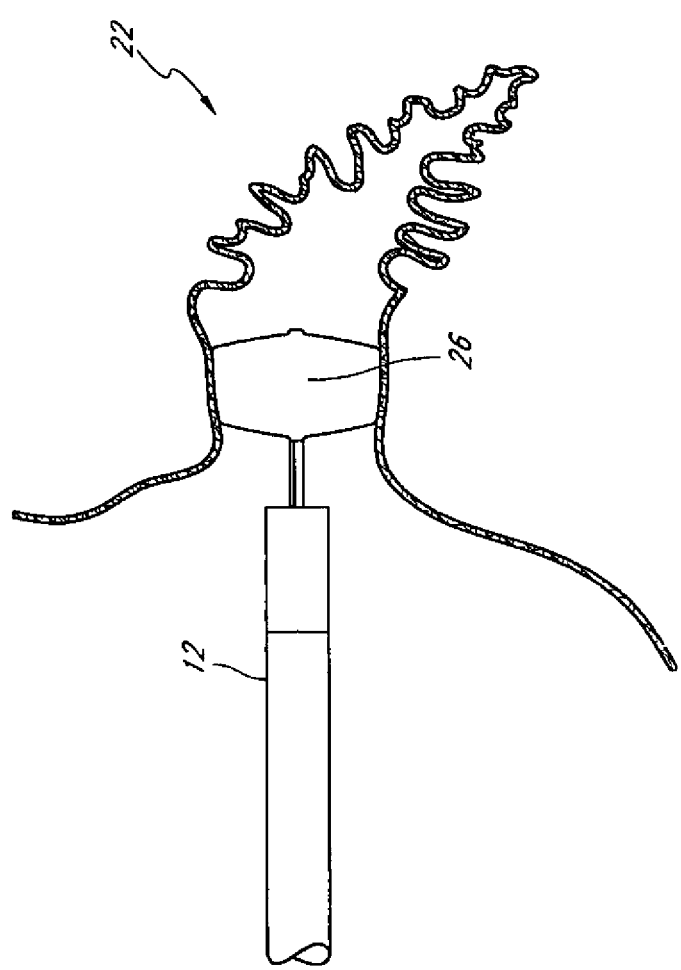
FIG. 29 is a cross-sectional view as in FIG. 25, with the implant expanded within the left atrial appendage.

In one embodiment, the balloon tip 68 may be deflated, so it no longer secures the distal end 14 of the sheath 12, when the implantable device 26 is near the distal end 14 of the sheath 12, but still within the sheath 12, as shown in FIG. 27. The sheath 12 may then be retracted proximally, and/or the implantable device 26 may be distally extended, to expose the implantable device 26, as illustrated in FIG. 28B. In another embodiment, the implantable device 26 may be advanced until it is completely or partially protruding from the sheath 12, as shown in FIG. 26B, then the balloon tip 68 may be deflated, as shown in FIG. 28A. The sheath may then be proximally retracted, as illustrated in FIG. 28B. The implantable device 26 may then be expanded using any of a variety of mechanism well known to those of skill in the art. In some embodiments, the implantable device 26 is self-expanding, and expands upon refraction of the sheath 12. FIG. 29 shows the implantable device 26 expanded within the LAA 22. Further steps may be employed for recapture and repositioning of the device by reinflation of the balloon 68 and repositioning of the transseptal sheath.

In some embodiments, the distal end of the transseptal sheath may be secured in place without using a balloon tip. For example, the distal end of the sheath may comprise ribs, hooks, barbs, anchors, bands, rings, or other friction devices to secure the distal end of the sheath in place.

Embodiments of the invention are used to treat other bodily openings, lumen and cavities, besides the left atrial appendage. For example, in some embodiments, the methods, devices and systems described herein are used to treat any heart opening or defect, such as a patent foramen ovale (PFO), an atrial septal defect (ASD), a ventricular septal defect (VSD), a patent ductus arteriosus (PDA), an aneurysm and/or an aortico-pulmonary window. Embodiments of the invention are also used during treatment of other conditions requiring the use of mitral valve leaflet clips, percutaneously implanted valves such as mitral or aortic valves, or during treatment of chordae tendonae for alteration of mitral valve prolapse.

In addition, while particular forms of the invention have been described, it will be apparent that various modifications can be made without departing from the spirit and scope of the invention. Accordingly it is not intended that the invention be limited to the particular embodiments described herein.

What is claimed is:

1. A method of delivering an implantable device to a left atrial appendage, comprising:
    delivering a first sheath comprising an elongate body having a central lumen sized and adapted to deliver an implantable device therethrough, a distal balloon located at a distal end thereof, and an inflation lumen operably connected to the distal balloon to a right atrium;
    advancing the first sheath distal end through an intraatrial septum and into a left atrium;
    inflating the distal balloon of the first sheath, thereby providing the first sheath with an atraumatic tip which extends distally beyond the distal end of the first sheath and radially therefrom;
    advancing the inflated distal balloon into the left atrial appendage and positioning a distal end of the distal balloon against a wall of the left atrial appendage;
    delivering an implantable device through the first sheath to the left atrial appendage;
    deflating said distal balloon; and
    removing said first sheath.

2. The method of claim 1, wherein the first sheath includes a distal end steerable from a proximal end of the first sheath without moving the proximal end of the first sheath.

3. The method of claim 2, wherein positioning includes steering the distal end of the first sheath from the proximal end of the first sheath.

4. The method of claim 1, wherein the distal balloon has a deflated configuration in which an inner diameter and an outer diameter of the distal balloon are generally equal to the corresponding diameters of the adjacent portion of the first sheath.

5. The method of claim 1, wherein inflating includes introducing saline into the distal balloon through the inflation lumen of the first sheath.

6. The method of claim 1, wherein inflating includes introducing a radiopaque fluid into the distal balloon through the inflation lumen of the first sheath.

7. The method of claim 1, wherein the method further includes:
    after positioning the distal end of the distal balloon against the wall of the left atrial appendage, further inflating the distal balloon.

8. The method of claim 1, wherein delivering the implantable device through the first sheath to the left atrial appendage includes advancing the implantable device to a position within the first sheath proximate the distal end thereof.

9. The method of claim 8, wherein deflating said distal balloon occurs when the implantable device is disposed at the position within the first sheath proximate the distal end thereof.

10. The method of claim 8, wherein removing said first sheath exposes the implantable device within the left atrial appendage.

* * * * *

UNITED STATES PATENT AND TRADEMARK OFFICE
CERTIFICATE OF CORRECTION

PATENT NO.         : 8,663,268 B2                          Page 1 of 1
APPLICATION NO.    : 13/403420
DATED              : March 4, 2014
INVENTOR(S)        : Chris Quinn and Jin Shimada It is certified that error appears in the above-identified patent and that said Letters Patent is hereby corrected as shown below:

In the Specification

Column 10
Line 35: delete "refraction" and insert therefor --retraction--.

Column 11
Line 31: delete "refraction" and insert therefor --retraction--.

Signed and Sealed this
Fifth Day of August, 2014

Michelle K. Lee
*Deputy Director of the United States Patent and Trademark Office*